US010161785B2

(12) United States Patent
Pepe et al.

(10) Patent No.: US 10,161,785 B2
(45) Date of Patent: Dec. 25, 2018

(54) METHOD OF MONITORING RUBBING BETWEEN A ROTARY PARTY AND A STATIONARY PART IN A ROTATING TURBOMACHINE, MONITORING ARRANGEMENT AND TURBOMACHINE

(71) Applicant: Nuovo Pignone SRL, Florence (IT)

(72) Inventors: Antonello Pepe, Florence (IT); Marzia Sepe, Florence (IT); Dario Nurzad, Florence (IT); Riccardo Garbin, Florence (IT)

(73) Assignee: NUOVO PIGNONE SRL, Florence (IT)

( * ) Notice: Subject to any disclaimer, the term of this patent is extended or adjusted under 35 U.S.C. 154(b) by 233 days.

(21) Appl. No.: 15/305,665

(22) PCT Filed: Apr. 22, 2015

(86) PCT No.: PCT/EP2015/058675
§ 371 (c)(1),
(2) Date: Oct. 21, 2016

(87) PCT Pub. No.: WO2015/162160
PCT Pub. Date: Oct. 29, 2015

(65) Prior Publication Data
US 2017/0044929 A1    Feb. 16, 2017

(30) Foreign Application Priority Data
Apr. 24, 2014  (IT) .............. CO2014A0014

(51) Int. Cl.
*G01H 1/00* (2006.01)
*F01D 21/00* (2006.01)
*F01D 21/04* (2006.01)

(52) U.S. Cl.
CPC ............. *G01H 1/003* (2013.01); *F01D 21/00* (2013.01); *F01D 21/04* (2013.01);
(Continued)

(58) Field of Classification Search
CPC ...................................................... G01H 1/006
(Continued)

(56) References Cited

U.S. PATENT DOCUMENTS

| 4,377,947 A | 3/1983 | Matsushita et al. |
| 4,478,082 A | 10/1984 | Sato et al. |

(Continued)

FOREIGN PATENT DOCUMENTS

| DE | 102012107421 A1 | 2/2013 |
| EP | 0 256 845 A2 | 2/1988 |

(Continued)

OTHER PUBLICATIONS

International Search Report and Written Opinion dated Jul. 28, 2015 which was issued in connection with PCT Patent Application No. PCT/EP2015/058675 which was filed on Apr. 22, 2015.

(Continued)

*Primary Examiner* — John Chapman, Jr.
(74) *Attorney, Agent, or Firm* — GE Global Patent Operation

(57) ABSTRACT

The arrangement for monitoring rubbing between a rotary part and a stationary part in a rotating turbomachine comprises at least one mechanical oscillations detector for measuring mechanical oscillations at at least one point of the turbomachine, at least one particles detector for measuring debris passing in at least one section of a flow path of the turbomachine, and an electronic monitoring unit electrically or electromagnetically connected to the oscillations detector and the particles detector, and arranged to acquire and process signals generated by the oscillations detector and the (Continued)

particles detector. The electronic monitoring unit uses the oscillations measurement primarily for estimating presence of rubbing and the debris measurement primarily for estimating severity of rubbing.

11 Claims, 3 Drawing Sheets

(52) U.S. Cl.
CPC .... *F05D 2220/32* (2013.01); *F05D 2270/114* (2013.01); *F05D 2270/334* (2013.01); *G01N 2291/2693* (2013.01)

(58) Field of Classification Search
USPC .............................................. 73/660, 112.01
See application file for complete search history.

(56) References Cited

U.S. PATENT DOCUMENTS

| | | | |
|---|---|---|---|
| 4,607,337 A | * | 8/1986 | Rosenbush .......... G01N 27/626 701/100 |
| 4,669,315 A | | 6/1987 | Sato et al. |
| 5,070,722 A | | 12/1991 | Hawman et al. |
| 6,668,655 B2 | | 12/2003 | Harrold et al. |
| 8,682,563 B2 | | 3/2014 | Malcolmson et al. |

FOREIGN PATENT DOCUMENTS

| | | |
|---|---|---|
| EP | 0 256 846 A2 | 2/1988 |
| EP | 1533479 A2 | 5/2005 |
| EP | 2273075 A2 | 1/2011 |
| EP | 2538199 A2 | 12/2012 |

OTHER PUBLICATIONS

Italian Search Report and Written Opinion dated Jul. 21, 2014 which was issued in connection with Italian Patent Application No. CO2014A000014 which was filed on Apr. 24, 2014.

* cited by examiner

METHOD OF MONITORING RUBBING BETWEEN A ROTARY PARTY AND A STATIONARY PART IN A ROTATING TURBOMACHINE, MONITORING ARRANGEMENT AND TURBOMACHINE

BACKGROUND

Embodiments of the subject matter disclosed herein relate to methods of monitoring rubbing between a rotary part and a stationary part in a rotating turbomachine, monitoring arrangements and turbomachines.

In general, rubbing in a rotating turbomachine is a problem, sometimes a severe problem.

Therefore, in the past, solutions have been conceived for detecting rubbing through acoustic sensors; for example, such solutions are described in U.S. Pat. No. 4,377,947 and U.S. Pat. No. 4,478,082.

Through the measurement of acoustic emission, it is difficult to understand whether rubbing is damaging the machine or not, which is problematic.

BRIEF DESCRIPTION

Therefore, there is a need for an improved way of monitoring rubbing.

An object of the present embodiments is to solve this problem by way of combining mechanical oscillations measurement with debris measurement. Debris may be due to various reasons, but if debris is measured after that rubbing is detected, it is highly likely that debris is caused by rubbing and therefore, in this case, rubbing may be considered severe and dangerous.

Furthermore, rubbing and its severity may depend on the operating mode of the turbomachine, for example "start-up", "shut-down", "crank", "loading", "inlet bleed heating", "washing", etc. Therefore, the rubbing presence estimation and/or the rubbing severity estimation may be based also on the operating mode of the machine.

A first aspect of the present invention is a method of monitoring rubbing.

The method of monitoring rubbing between a rotary part and a stationary part in a rotating turbomachine comprises measuring mechanical oscillations at at least one point of the turbomachine; and measuring debris passing in at least one section of a flow path of the turbomachine. The oscillations measurement is used for estimating presence of rubbing, and the debris measurement is used for estimating severity of rubbing.

A second aspect of the present invention is an arrangement for monitoring rubbing.

The arrangement for monitoring rubbing between a rotary part and a stationary part in a rotating turbomachine comprises at least one mechanical oscillations detector, at least one particles detector, and an electronic monitoring unit electrically or electromagnetically connected to the at least one oscillations detector and the at least one particles detector, and arranged to acquire and process signals generated by the at least one oscillations detector and the at least one particles detector.

A third aspect of the present invention is a turbomachine.

The turbomachine comprises an arrangement for monitoring rubbing between a rotary part and a stationary part in the turbomachine when rotating as set out above.

BRIEF DESCRIPTION OF DRAWINGS

The accompanying drawings, which are incorporated herein and constitute a part of the specification, illustrate exemplary embodiments of the present invention and, together with the detailed description, explain these embodiments. In the drawings.

DETAILED DESCRIPTION

The following description of exemplary embodiments refers to the accompanying drawings.

The following description does not limit the embodiments of the present invention that, in particular, are not limited to combustion gas turbine engines and to their high-flow online washing although these are typical applications thereof. Instead, the scope of the present application is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
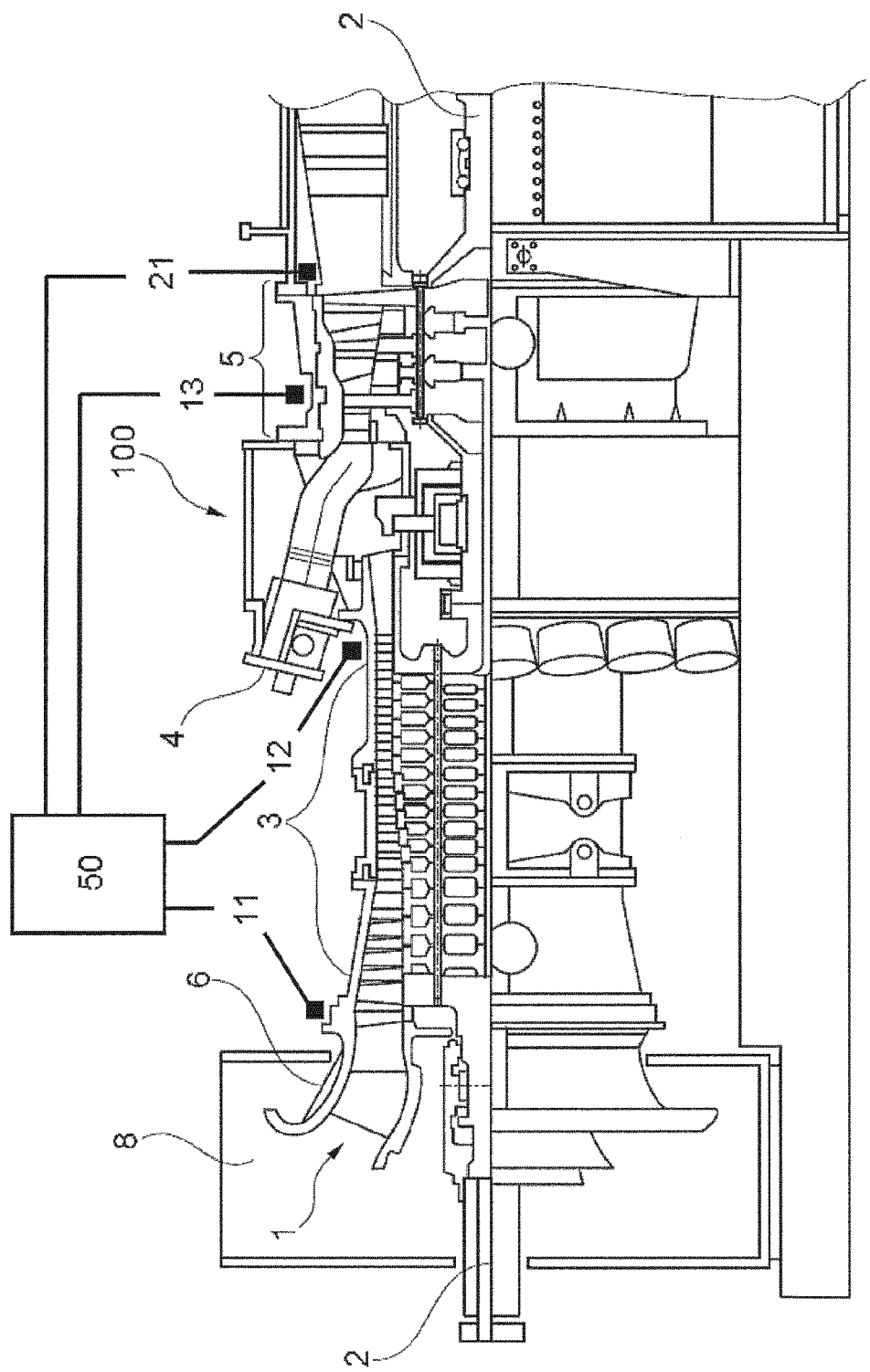
FIG. 1 shows a simplified view of an embodiment of a combustion gas turbine engine (the upper half is shown in cross-section)

With reference to FIG. 1 there is shown a combustion gas turbine engine generally designated with the reference number 100. The arrow 1 represent the air flow entering the bellmouth of the engine 100. The basic elements of a gas turbine engine are the compressor 3, the combustors 4 and the turbine 5. The engine 100 includes a shaft 2 that drives the blades of the compressor 3. The compressed air is heated by the combustors 4 and the resulting hot gases expand driving the blades of the turbine 5 thus rotating the shaft 2. Included in the combustion gas turbine engine 100 there is also a starter motor (not shown) that serves the purpose of operating the gas turbine engine at startup and during off-line washing procedures.

Combustion gas turbine engines draw huge quantity of air containing particles that can contaminate the compressor blades and vanes. Before entering the gas turbine engine, the air must be filtered in order to remove the greatest part of air particles that can contribute to fouling. A FOD screen is located in a plenum chamber 8 at the entrance of the gas turbine engine in order to stop those particles that can damage primarily the blades and vanes of the compressor 3.

Despite the use of filters, it is difficult to avoid completely the deposition and accumulation of particles on the blades and vanes of the compressor, thus it is necessary to resort to periodic washing operations in order to restore the original levels of efficiency.

The washing operations are accomplished through a series of nozzles that spray atomized washing fluid, normally water, in the interior of the gas turbine engine.

Figure 3:
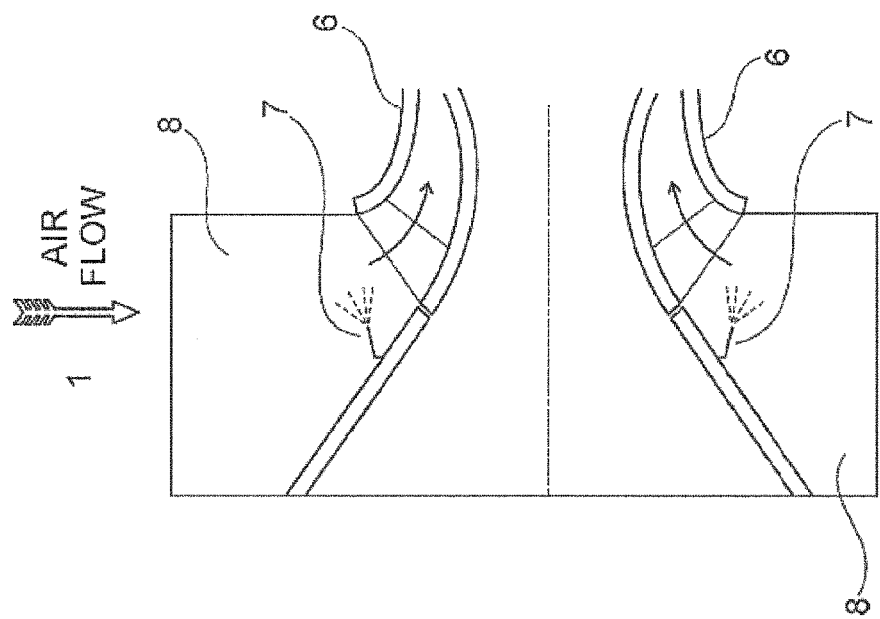
FIG. 3 shows a longitudinal cross-sectional view of the inlet zone of the combustion gas turbine engine of FIG. 1.
Figure 2:
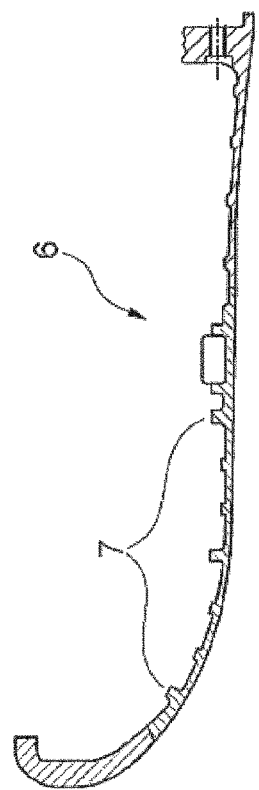
FIG. 2 shows a longitudinal cross-sectional view of a bellmouth of the combustion gas turbine engine of FIG. 1.

FIG. 2 and FIG. 3 show details of a known washing system.

In FIG. 2 the nozzles 7 are installed in the bellmouth 6 of the gas turbine engine, in particular in the region identified by reference numeral.

FIG. 3 shows the inlet portion of a combustion gas turbine engine where air enters radially (coming from an upper opening) and the nozzles 7 are installed on an internal radial volute (radially opposite to the bellmouth 6). The nozzles are positioned in such a way that the washing fluid can enter and penetrate the compressor, moving through it towards the exit of the machine and washing the fouling thanks to the fact that during the washing operation the rotor is rotating 1) at low speed driven by the starter engine in case of offline washing or it is rotating 2) at full load in case of online washing.

FIG. 1 shows schematically a first mechanical oscillations detector 11 located at the inlet of the compressor 3, a second mechanical oscillations detector 12 located at the outlet of the compressor 3, a third mechanical oscillations detector 13 located at the inlet of the turbine 5, and a particles detector 21 located at the outlet or exhaust of the turbine 5, i.e. at the outlet of the engine 100, that measures particles passing in the outlet.

An electronic monitoring unit 50 is electrically or electromagnetically connected to the oscillations detectors 11, 12, 13 and the particles detector 21, and is arranged to acquire and process signals generated by these detectors. In FIG. 1, the connections are wired; anyway, alternatively, one or more or all of them may be a wireless connection or the combination of a wired connection and a wireless connection.

The combustion gas turbine engine 100 has a plurality of operating modes, for example: "start-up", "shut-down", "crank", "loading", "inlet bleed heating", "washing" (that may be split into "offline washing" and "online washing").

In order to monitor rubbing between a rotary part and a stationary part in a turbomachine, for example the combustion gas turbine engine 100 of FIG. 1, when it rotates, essentially the following two steps are carried out: measuring mechanical oscillations at at least one point of the turbomachine, and measuring debris passing in at least one section of a flow path of the turbomachine.

The oscillations measurement is used by the unit 50 (primarily) for estimating presence of rubbing, and the debris measurement is used by the unit 50 (primarily) for estimating severity of rubbing; the quantity in the unit of time (for example per second or per minute) of particles detected is considered related to the degree of the occurring rubbing. It is to be noted that rubbing presence may be estimated using both oscillations measurement and debris measurement; in other words, debris measurement may be used by unit 50 also for estimating presence of rubbing.

Step A may consider oscillations in a first range of frequencies, typically between 0 Hz and 100 kHz, that are usually called "vibrations", and/or in a second range frequencies, typically between 100 kHz and 2 MHz, that are usually called "acoustic emissions". Devices suitable for detecting oscillations in the first range are usually called "acceleration sensors"; devices suitable for detecting oscillations in the second range are usually called "acoustic sensors" or "acoustic emission sensors".

Step B is carried out for example through a "capacitive sensor".

As in the embodiment of FIG. 1, mechanical oscillations may be measured at a set of points of the turbomachine.

Having a plurality of oscillations measurements carried out at the same time and at different points may allow also to estimate location of rubbing; this requires appropriate processing by the unit 50.

As in the embodiment of FIG. 1, a place to detect particles is at an outlet of the turbomachine; in this way, it is likely that any possible debris generated during operation of the turbomachine is measured.

It is possible to measure debris passing in a set of sections (for example two or three) of a flow path of the turbomachine. For example, in the embodiment of FIG. 1, a first particles detector may be located at the inlet of the compressor 3 and may detect particles entering the turbomachine. A second particles detector may be located at the outlet of the compressor 3 and may detect particles due to rubbing inside the compressor. A third particles detector may be located at the outlet or exhaust of the turbine 5 (the third particles detector corresponds to detectors 21) and may detect particles due to rubbing inside the turbine.

As already explained, it may be beneficial that rubbing severity estimation is carried out if rubbing presence estimation is positive; and this should avoid that particles due to other reasons are erroneously considered.

In order to achieve a reliable and meaningful monitoring of rubbing, in an embodiment, the operating mode of the turbomachine is preliminary considered, and the rubbing presence estimation and/or the rubbing severity estimation is based also on the operating mode. In fact, in some operating modes rubbing is more likely and, to a certain degree, expected; in other operating modes rubbing should not occur at all. For example, the rubbing presence estimation and/or the rubbing severity estimation may be based also on a comparison between one or more measured physical quantities and one or more baselines relating to current operating mode. A baseline should be determined based on tests on and/or simulations of the turbomachine.

One of the operating modes of a turbomachine, in particular a combustion gas turbine engine like the one of FIG. 1, that is more likely to cause rubbing is the online washing operating mode, in particular when it is carried out with high mass flow of detergent substance (often a liquid substance, typically water).

According to an embodiment of the present invention, rubbing is monitored in a combustion gas turbine engine when the detergent liquid substance is sprayed so that the liquid-to-gas ratio at the inlet of the compressor is more than 1% and less than 5% (i.e. "high-flow") with reference to the rated mass flow of the compressor; in order to achieve this result, the detergent liquid substance may be sprayed at a pressure of more than 0.2 MPa and less than 2.0 MPa.

Rubbing monitoring may be carried out for example only during washing or for example only during online washing or for example only during high-flow online washing.

The arrangement for monitoring rubbing according to an embodiment comprises one or more mechanical oscillations detector, one or more particles detector, and an electronic monitoring unit.

The electronic monitoring unit may be for example a PC or the combination of a PC and one or more data acquisition boards; the PC may be close to the turbomachine or may be remote.

Such rubbing monitoring arrangement may be integrated in a turbomachine.

Such rubbing monitoring arrangement may be part of a monitoring equipment that takes care of various kinds of monitoring; for example, vibrations sensors may be used for monitoring vibrations due to reasons different from rubbing.

FIG. 4 shows exemplary and simplified flow charts corresponding to activities carried out by the electronic monitoring unit 50 of FIG. 1.

Figure 4A:
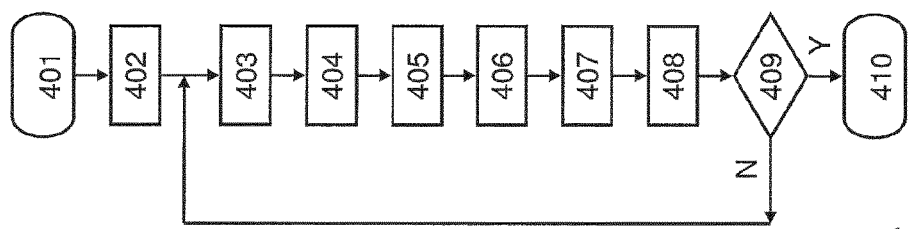
FIG. 4 shows exemplary and simplified flow charts corresponding to activities carried out by the electronic monitoring unit of FIG. 1.
Figure 4B:
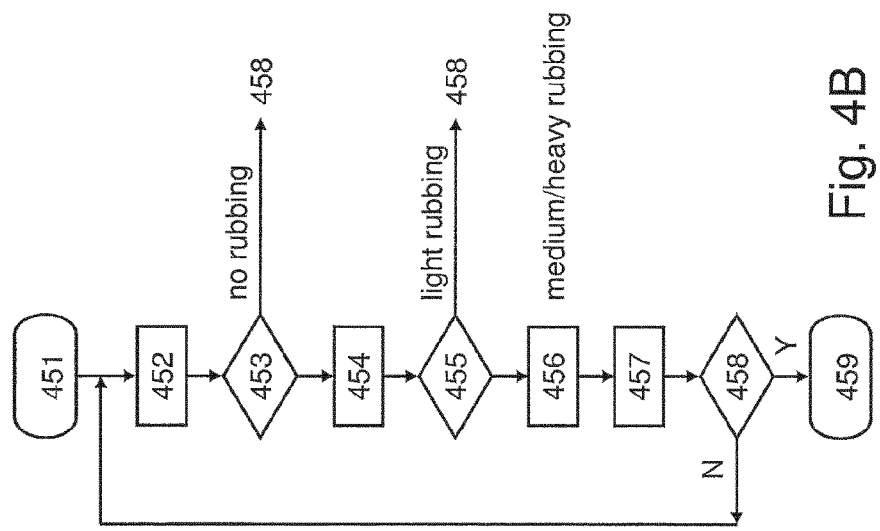

FIG. 4A relates to data acquisition and storage and FIG. 4B relates to data use and processing. These two sets of activities are typically carried out in parallel by unit 50; for example, data acquisition and storage activities may be carried out by one or more data acquisition boards and data use and processing activities may be carried out by a PC.

In the flow chart of FIG. 4A, the following steps are shown:
- step 401: start of data acquisition and storage,
- step 402: storing baselines data—this is typically carried out for each operating mode of the turbomachine in conditions that are supposed to be without rubbing,
- step 403: acquiring current operating mode data,
- step 404: storing current operating mode data,
- step 405: acquiring current oscillations data,
- step 406: storing current oscillations data,
- step 407: acquiring current passing particles data,
- step 408: storing current passing particles data,
- step 409: checking a stop-monitoring command, if Yes proceeding with step 410 if Not proceeding with step 403,
- step 410: stop of data acquisition and storage.

In the flow chart of FIG. 4B, the following steps are shown:
- step 451: start of data use and processing,
- step 452: analyzing current oscillations data and comparing with corresponding baseline or baselines of the current operating mode,
- step 453: checking comparison, if data are close to baseline(s) the estimation is "no rubbing" and proceeding with step 458, otherwise proceeding with step 454,
- step 454: analyzing current passing particles data and comparing with corresponding baseline or baselines of the current operating mode,
- step 455: checking comparison, if data are close to baseline(s) the estimation is "low rubbing"/"light rubbing" and proceeding with step 458, otherwise proceeding with step 456,
- step 456: processing current passing particles and corresponding baseline(s) and estimating whether there is a "medium rubbing" or "high rubbing"/"heaving rubbing", the estimation may be signaled (through audio and/or video) to a local or remote operator, in case of "high rubbing" a safety measure may be automatically taken,
- step 457: processing current oscillations data and possibly current passing particles data and localizing rubbing within the turbomachine, the localization may be displayed to a local or remote operator,
- step 458: checking a stop-monitoring command, if Yes proceeding with step 459 if Not proceeding with step 452,
- step 469: stop of data use and processing.

It is to be understood that even though numerous characteristics and advantages of various embodiments have been set forth in the foregoing description, together with details of the structure and functions of various embodiments, this disclosure is illustrative only, and changes may be made in detail, especially in matters of structure and arrangement of parts within the principles of the embodiments to the full extent indicated by the broad general meaning of the terms in which the appended claims are expressed. It will be appreciated by those skilled in the art that the teachings disclosed herein can be applied to other systems without departing from the scope and spirit of the application.

What is claimed is:

1. A method of monitoring rubbing between a rotary part and a stationary part in a rotating turbomachine, the method comprising:
   measuring mechanical oscillations at at least one point of the turbomachine; and
   measuring debris passing in at least one section of a flow path of the turbomachine;
   wherein at least one oscillations measurement is used for estimating presence of rubbing; and
   wherein at least one debris measurement is used for estimating severity of rubbing.

2. The method of claim 1, wherein mechanical oscillations are measured at a set of points of the turbomachine, wherein oscillations measurements at the set of points are used for estimating a location of rubbing.

3. The method of claim 1, wherein debris is measured at an outlet of the turbomachine.

4. The method of claim 1, wherein rubbing severity estimation is carried out if rubbing presence estimation is positive.

5. The method of claim 1, further comprising determining an operating mode of the turbomachine, wherein the rubbing presence estimation and/or the rubbing severity estimation are/is based on the determined operating mode.

6. The method of claim 1, wherein the turbomachine is in an online washing operating mode with high mass flow of detergent substance.

7. The method of claim 1, wherein the turbomachine is a combustion gas turbine engine.

8. An arrangement for monitoring rubbing between a rotary part and a stationary part in a rotating turbomachine, the arrangement comprising:
   at least one mechanical oscillations detector;
   at least one particles detector; and
   an electronic monitoring unit electrically or electromagnetically connected to the at least one oscillations detector and the at least one particles detector, and arranged to acquire and process signals generated by the at least one oscillations detector and the at least one particles detector.

9. The arrangement of claim 8, further comprising a set of vibrations detectors electrically or electromagnetically connected to the electronic monitoring unit.

10. A turbomachine comprising:
    an arrangement for monitoring rubbing between a rotary part and a stationary part in the turbomachine when rotating the arrangement comprising:
    at least one mechanical oscillations detector;
    at least one particles detector; and
    an electronic monitoring unit electrically or electromagnetically connected to the at least one oscillations detector and the at least one particles detector, and arranged to acquire and process signals generated by the at least one oscillations detector and the at least one particles detector.

11. The turbomachine of claim 10, further comprising a set of vibrations detectors electrically or electromagnetically connected to the electronic monitoring unit.

* * * * *